(12) United States Patent
Bradley et al.

(10) Patent No.: US 8,858,560 B2
(45) Date of Patent: Oct. 14, 2014

(54) ARTHROSCOPIC HARVESTING AND THERAPEUTIC APPLICATION OF BONE MARROW ASPIRATE

(75) Inventors: James P. Bradley, Pittsburgh, PA (US);
Reinhold Schmieding, Naples, FL (US);
Ashley Willobee, Naples, FL (US); J. Maxwell Teets, Cleveland, OH (US)

(73) Assignee: Arthrex, Inc., Naples, FL (US)

( * ) Notice: Subject to any disclaimer, the term of this patent is extended or adjusted under 35 U.S.C. 154(b) by 1638 days.

(21) Appl. No.: 11/892,495

(22) Filed: Aug. 23, 2007

(65) Prior Publication Data

US 2008/0221527 A1  Sep. 11, 2008

Related U.S. Application Data

(60) Provisional application No. 60/839,411, filed on Aug. 23, 2006.

(51) Int. Cl.
| | | |
|---|---|---|
| *A61F 2/46* | (2006.01) | |
| *A61L 27/48* | (2006.01) | |
| *A61L 27/26* | (2006.01) | |
| *A61L 27/36* | (2006.01) | |
| *A61L 27/50* | (2006.01) | |
| *A61B 10/02* | (2006.01) | |
| *A61B 17/34* | (2006.01) | |
| *A61F 2/28* | (2006.01) | |
| *A61M 5/19* | (2006.01) | |

(52) U.S. Cl.
CPC ....... *A61B 10/025* (2013.01); *A61B 2010/0258* (2013.01); *A61F 2002/4649* (2013.01); *A61L 27/48* (2013.01); *A61L 27/26* (2013.01); *A61B 17/3472* (2013.01); *A61L 27/3608* (2013.01); *A61F 2002/2867* (2013.01); *A61F 2/4601* (2013.01); *A61L 27/50* (2013.01); *A61M 5/19* (2013.01)
USPC ........................................ 606/86 R; 606/232

(58) Field of Classification Search
USPC ........................................ 606/86 R, 95, 232
See application file for complete search history.

(56) References Cited

U.S. PATENT DOCUMENTS

| | | | |
|---|---|---|---|
| 2002/0122790 A1* | 9/2002 | Hunziker | 424/93.7 |
| 2002/0161449 A1* | 10/2002 | Muschler | 623/23.51 |
| 2003/0225364 A1* | 12/2003 | Kraft et al. | 604/35 |
| 2004/0078090 A1* | 4/2004 | Binette et al. | 623/23.76 |
| 2007/0191849 A1 | 8/2007 | ElAttrache et al. | |

OTHER PUBLICATIONS

Cengage, Gale, "A Cartilage Transfusion for Bad Knees," Business Week, Apr. 10, 1995, p. 103.*

* cited by examiner

*Primary Examiner* — Nicholas Woodall
*Assistant Examiner* — Christine Nelson
(74) *Attorney, Agent, or Firm* — Dickstein Shapiro LLP

(57) ABSTRACT

Methods of arthroscopic harvesting of bone marrow aspirate from bone joints and therapeutic application of the bone marrow aspirate in a bone joint. The method of harvesting includes extracting bone marrow from a joint, adding a biomaterial, and adding clotting agent to form a clot.

8 Claims, 18 Drawing Sheets

ARTHROSCOPIC HARVESTING AND THERAPEUTIC APPLICATION OF BONE MARROW ASPIRATE

CROSS-REFERENCE TO RELATED APPLICATIONS

This application claims priority to U.S. Provisional Application Nos. 60/839,411, filed on Aug. 23, 2006, the entire disclosure of which is hereby incorporated by reference.

FIELD OF THE INVENTION

The present invention relates to methods of arthroscopic surgery and, more specifically, to an improved method of arthroscopic harvesting of bone marrow aspirate from the joints of long bones, and therapeutic usage of the aspirated bone marrow aspirate in the same joint.

BACKGROUND OF THE INVENTION

Bone marrow, which is found in the long bones and the iliac crest, contains stem cells that differentiate into mature blood cells. Bone marrow may be aspirated from the bones and used as a way to localize stem cells at the site of injury. For example, bone marrow aspirate ("BMA") can be applied to a biomaterial, such as an allograft patch, a collagen patch, or synthetic materials such as hyaluronic acid ("HA"), calcium phosphate, or polymer, and delivered in vivo at the site of injury to aid in repair or replace damaged tissue.

In prior known techniques for delivering BMA to a surgical site, bone marrow has been harvested from the iliac crest. Thus, an additional surgical site for aspiration of the bone marrow is required beyond the site of the surgical repair. Currently there is no known method for aspirating and applying bone marrow from and to the same site as the surgery using arthroscopic techniques.

DETAILED DESCRIPTION OF THE INVENTION

Figure 1:
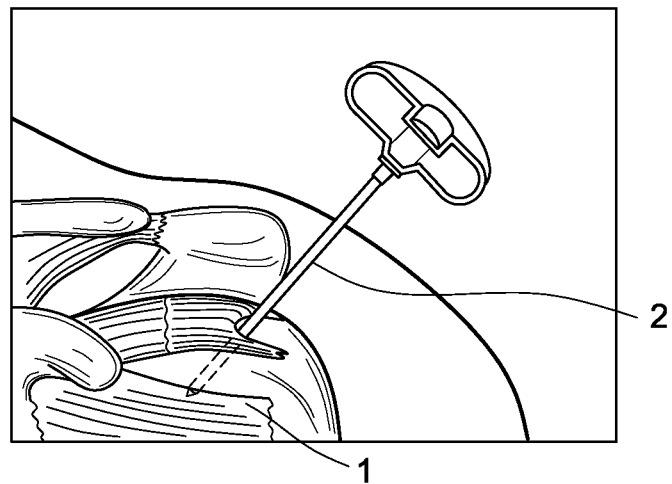
FIGS. 1-7 illustrate the sequence steps for bone marrow aspiration from a human shoulder, according to a preferred embodiment of the present invention.

Referring now to the drawings, where like elements are designated by like reference numerals, FIGS. 1-31 illustrate a method of arthroscopic bone marrow harvesting combined with attaching a tendon to bone according to the present invention. For exemplary purposes only, the invention will be described below with reference to an arthroscopic rotator cuff tendon repair. However, the invention is not limited to this exemplary embodiment and has applicability to any reattachment of soft tissue to bone or tissue to tissue or bone to bone.

The method of the present invention enhances arthroscopic harvesting of bone marrow aspirate from the joints of long bones, such as a hip joint, or an elbow joint, with subsequent therapeutic usage of extracted BMA in the same limb respective to the harvest site location. The result is a quick repair with a minimal number of sites for surgery and aspiration.

FIG. 1 illustrates a side view of a human shoulder of a patient undergoing arthroscopic bone marrow harvesting. First, a hollow, sharp-pointed trocar (not shown), which is included in a Bone Marrow Aspirate Kit, AR-1001DS, sold by Arthrex, Inc. of Naples, is used to puncture the tissue. A bone marrow aspiration needle 2 is disposed within the trocar. The aspiration needle 2 is inserted into a proximal humeral head 1, posterior intra-articularly.

Figure 2:
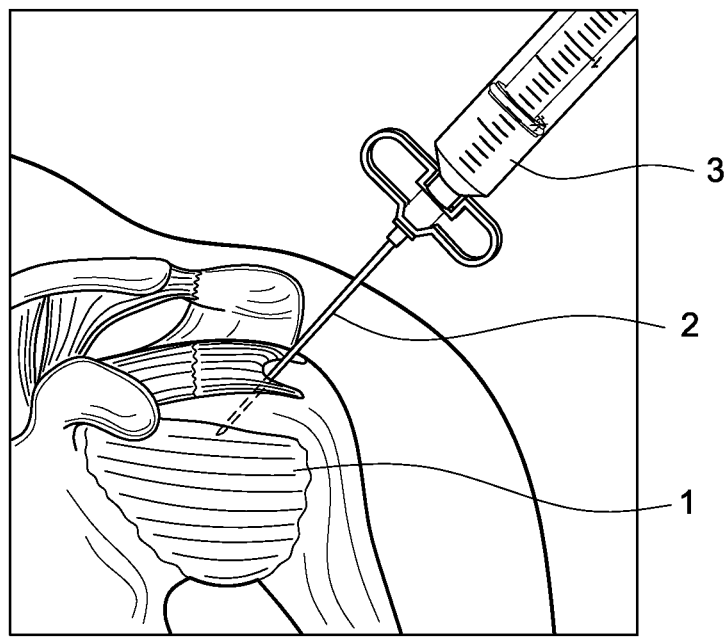

As illustrated in FIG. 2, once the trocar is removed, a syringe 3, for example, a 60 cc syringe to generate ample suction, is connected to the bone marrow aspiration needle 2 to draw the bone marrow. The aspiration needle 2 is redirected by rotating it by 180° after every 2-3 cc's has been extracted. The aspiration needle 2 is retracted posteriorly by about 1 cm and the above steps for extracting the bone marrow is repeated until about 10-20 cc's have been withdrawn into the syringe. Thus, about 10-20 cc's of bone marrow is aspirated.

In an alternative embodiment, arthroscopic bone marrow harvesting may be performed on a human knee of a patient. First, a drill bit of almost similar size of a bone marrow aspiration needle is used to make an entry hole by approaching the intercondylar notch of a distal femur through a lateral portal just below the superior aspect of the notch. Next, the aspiration needle is inserted into the medullary canal of the femur. A syringe, for example, a 60 cc syringe to generate ample suction, is connected to the bone marrow aspiration needle to draw the bone marrow. The aspiration needle is redirected by rotating it by 180° after every 2-3 cc's has been extracted. The aspiration needle is retracted anteriorly by about 1 cm and the above steps for extracting the bone marrow is repeated until about 10-20 cc's have been withdrawn into the syringe. Thus, about 10-20 cc's of bone marrow is aspirated.

Figure 3:
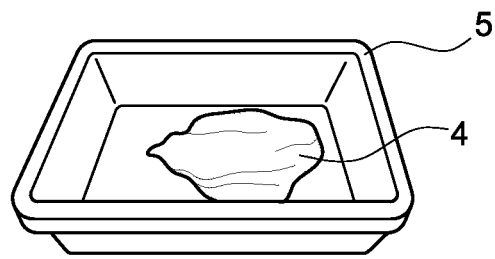

As shown in FIG. 3, the extracted bone marrow aspirate 4 is extracted from the syringe 3 (FIG. 2) into a sterile mixing bowl or prep tray 5 with a biomaterial, such as a collagen patch, sold by Arthrex, Inc., under the tradename Bio-Sponge™, and the collagen patch is hydrated with the extracted BMA. A clotting agent such as calcium salts and/or thrombin may be optionally added to the prep tray to initiate a clotting cascade.

Alternatively, the harvested bone marrow 4 may be separated and concentrated using a centrifugation technique. First, the bone marrow 4 must be transferred to a centrifuge tube (not shown) then centrifuged at various speeds and times (i.e., 1100 rcf for 6 minutes). The red blood cells are discarded and the buffy coat and plasma fractions are retained. Next, a biomaterial like a collagen patch, allograft patch, demineralized bone matrix ("DBM"), or synthetic material is added into the retained fraction of bone marrow. For example, a 10% calcium chloride solution is added to the fractionated blood at a 1:50 v/v ratio. The plasma, buffy coat, biomaterial, and calcium chloride mixture are then centrifuged a second time (e.g., 1500 rcf for 15 minutes). A clot then adheres to the patch.

Figure 4:
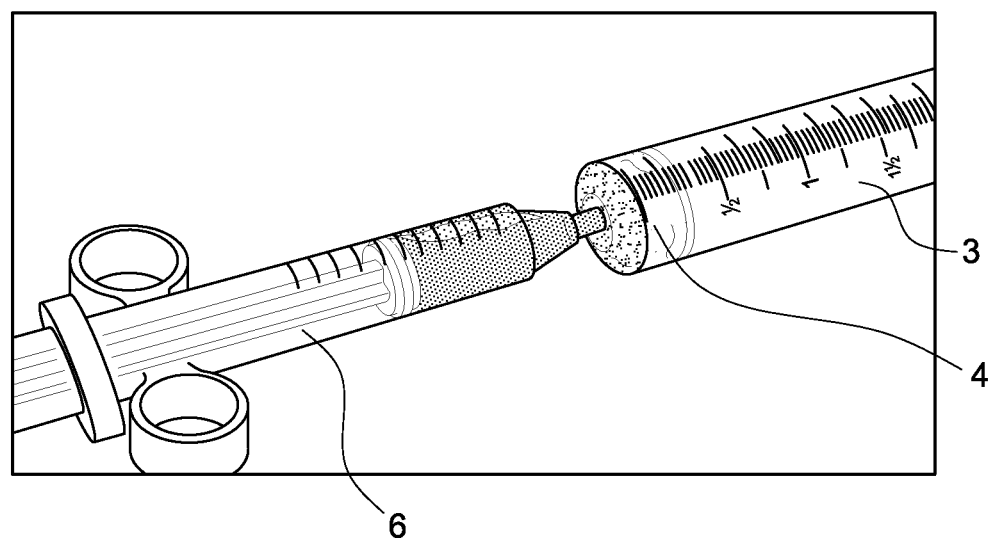
Figure 5:
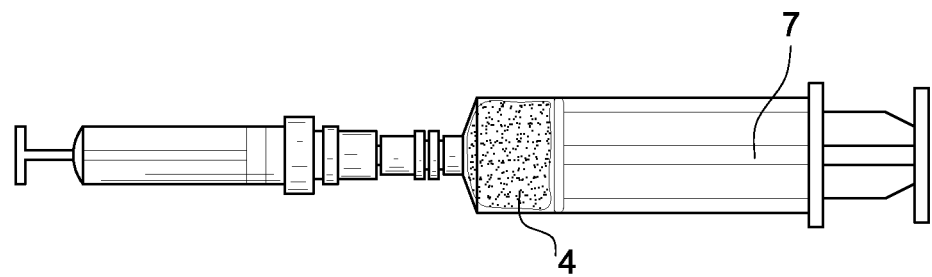
Figure 6:
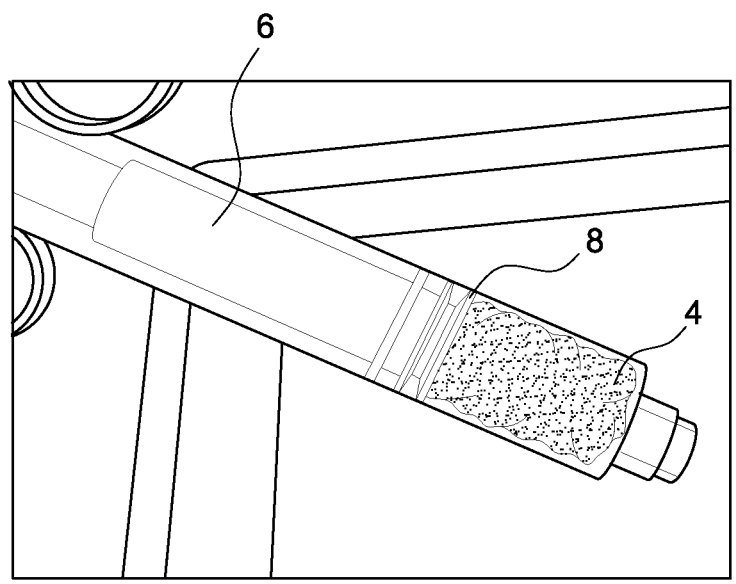
Figure 7:
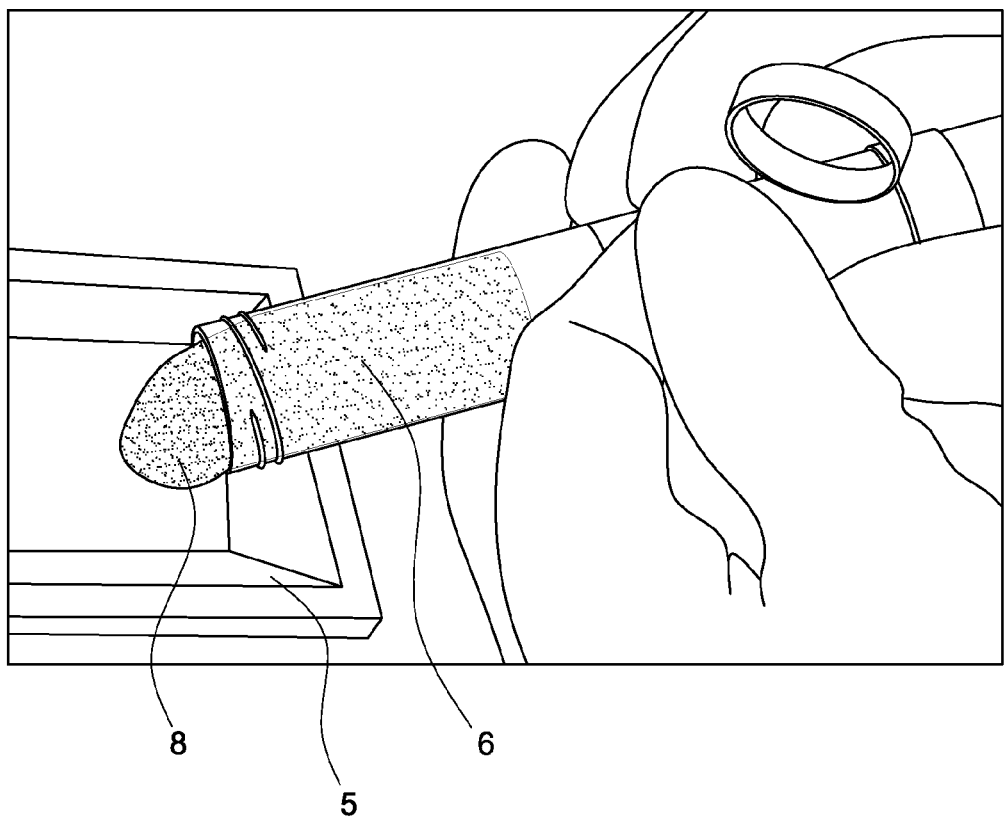

In an alternate embodiment, the extracted BMA may be transferred and delivered using an end-to-end syringe. FIG. 4 illustrates the direct transfer of BMA 4 into a second syringe 6 filled with DBM. Alternatively, as shown in FIG. 5, BMA 4 may be transferred into an empty screw top syringe 7. As illustrated in FIGS. 6 and 7, the BMA 4 forms a clot 8, once a clotting agent is added, in the second syringe 6 after 2-40 minutes, depending on clotting agent. The clot 8 is then delivered to the injured tissue or to a collagen patch.

The screw top syringe 7 (FIG. 5) is advantageous for BMA 4 transfer because it has a twist off cap that allows a surgeon to remove the clot 8 and add any types of biomaterial to the syringe. This syringe 7 can also be centrifuged. The clot/biomaterial composite is then delivered to the injured tissue to help promote healing.

Figure 8:
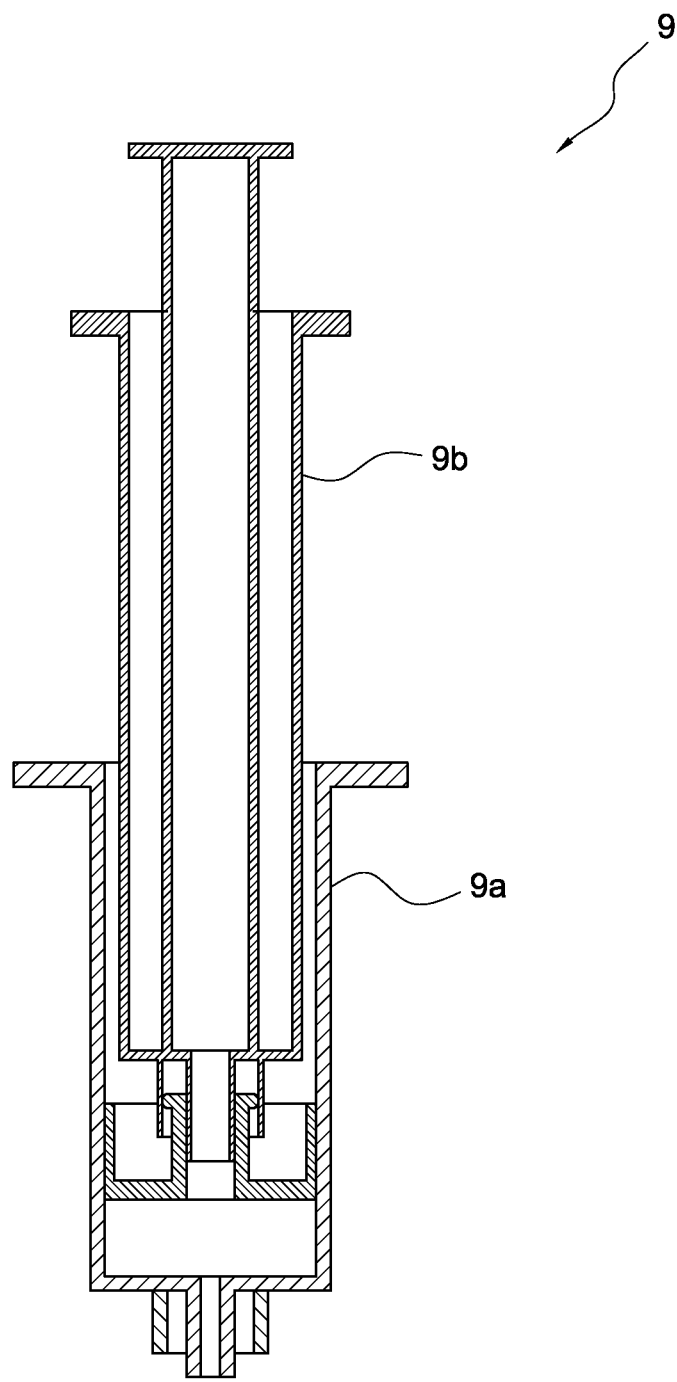
FIGS. 8-14 illustrate the sequence steps for using a double syringe to transfer and deliver extracted bone marrow aspirate, according to a preferred embodiment of the present invention.
Figure 9:
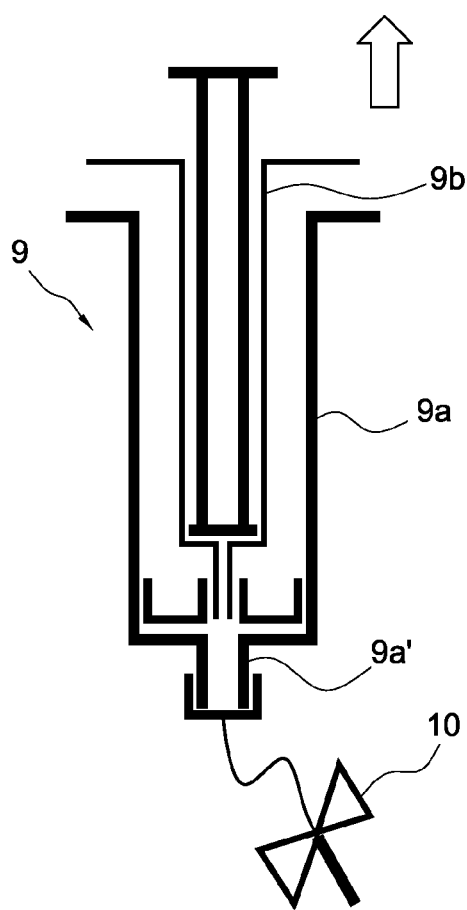
Figure 10:
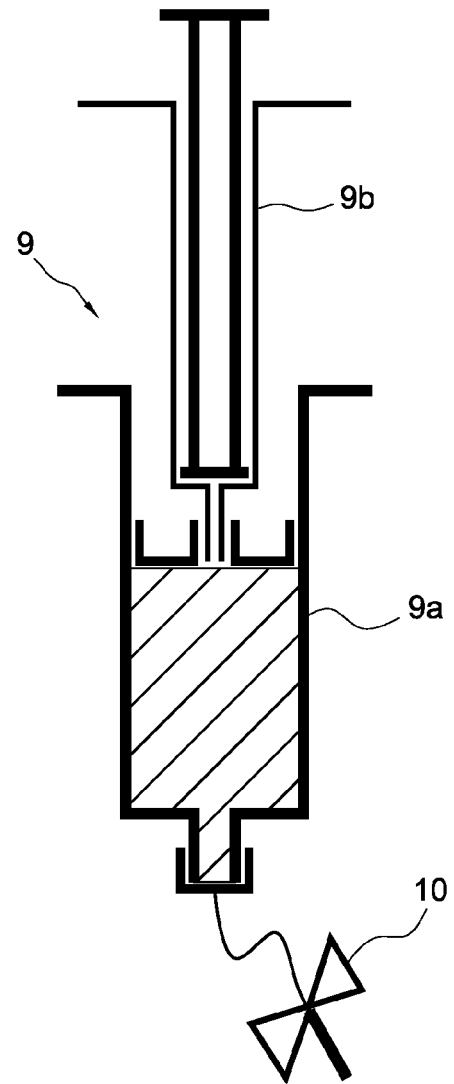
Figure 11:
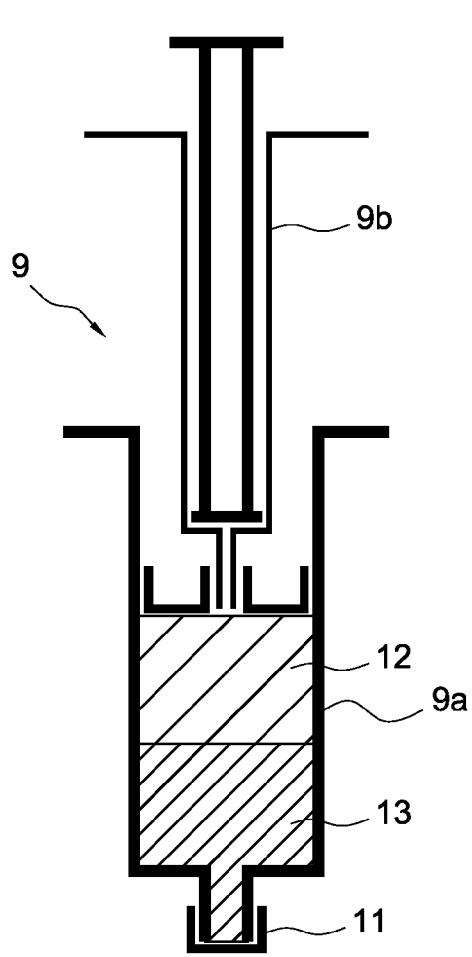
Figure 12:
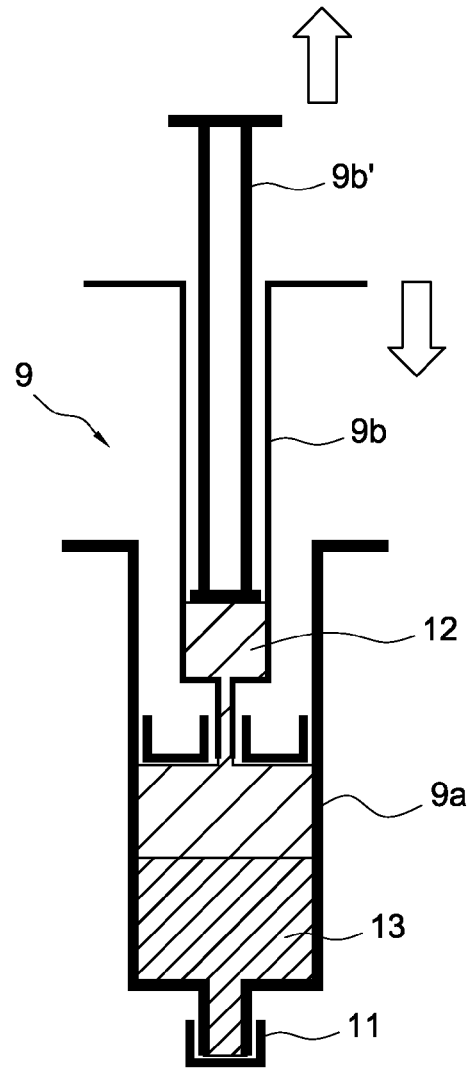
Figures 13, 14:
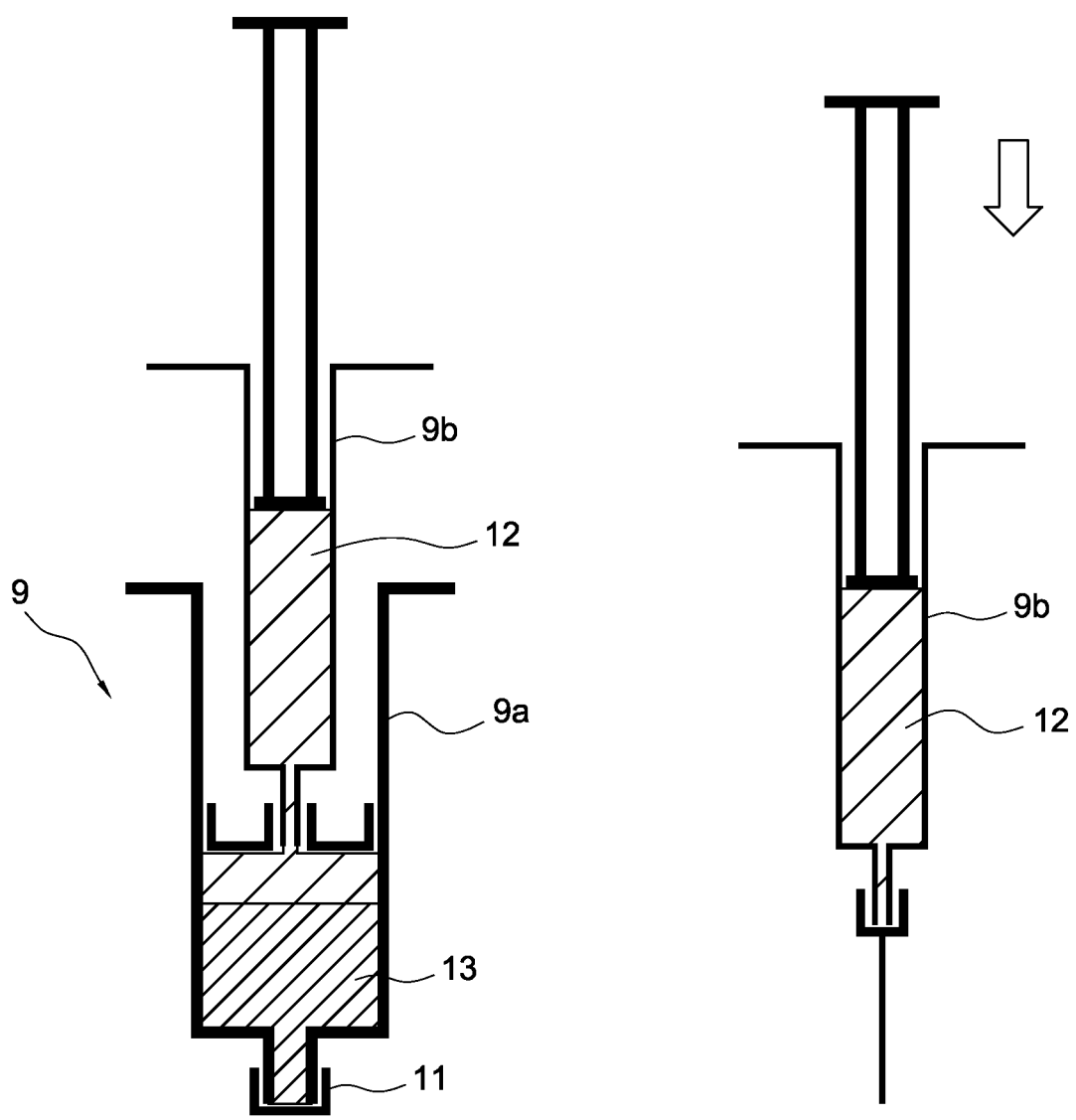

Another alternate embodiment provides the use of a double syringe 9 as shown in FIG. 8 to transfer and deliver the extracted BMA 4 (FIG. 3). The double syringe 9 comprises an inner syringe 9b and an outer syringe 9a. As shown in FIG. 9, a butterfly-cannula 10 is attached to a hole 9a' of the double syringe 9. The double syringe 9 is used to aspirate the bone marrow by moving the inner syringe 9b away from the hole 9a', as illustrated in FIG. 10. An anticoagulant, for example, heparin, sodium citrate, citrate or phosphate dextrose, is added to the bone marrow to keep it from clotting. The butterfly-cannula 9 (FIG. 9) is then replaced by a luer lock cap 11 and the syringe 9 is centrifuged to separate the plasma 12 from the red blood cells 13, as shown in FIG. 11. Next, as shown in FIG. 13, the plasma 12 is transferred into the smaller syringe 9b by moving the piston 9b' away from the outer syringe 9a. Once the transfer is complete as shown in FIG. 13, the double syringe 9 is separated by removing the inner syringe 9b as shown in FIG. 14. The plasma 12 can then be used to form a clot as discussed in detail above. Then, the clot can be delivered to the injured tissue, an allograft (AlloBridge™), or to a collagen patch (BioSponge™).

In yet another embodiment, the double syringe 9 is used to aspirate the bone marrow by moving the inner syringe 9b away from the hole 9a', as illustrated in FIG. 10. A clotting agent, for example, calcium salt or thrombin, is added to the bone marrow to form a clot. The butterfly-cannula 9 (FIG. 9) is then replaced by a luer lock cap 11 and the syringe 9 is centrifuged to separate the serum (not shown). The serum can then be delivered to the injured tissue, an allograft (AlloBridge™), or to a collagen patch (BioSponge™).

Figure 15:
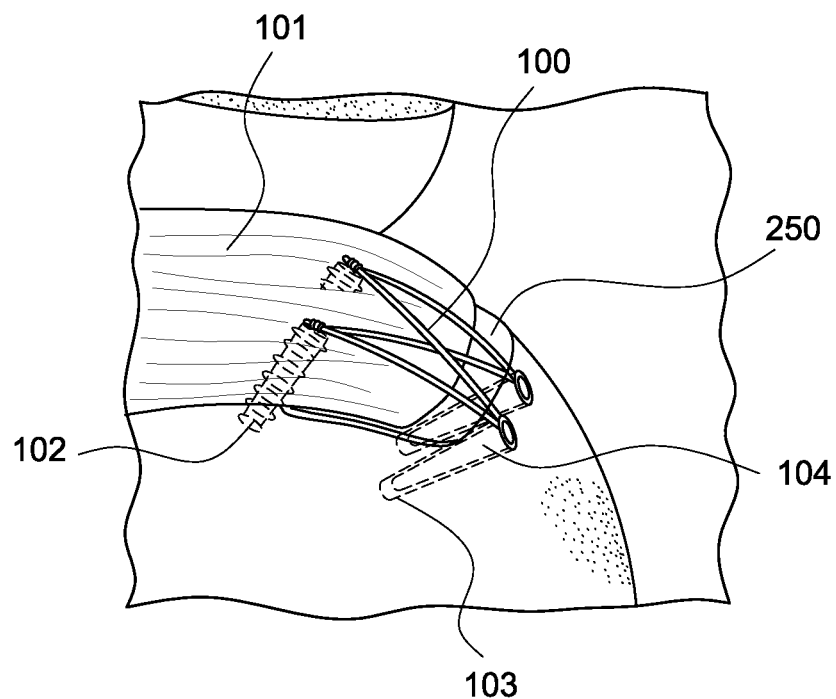
FIGS. 15-16 are schematic diagrams of a human shoulder illustrating a reattachment technique for rotator cuff repair.
Figure 16:
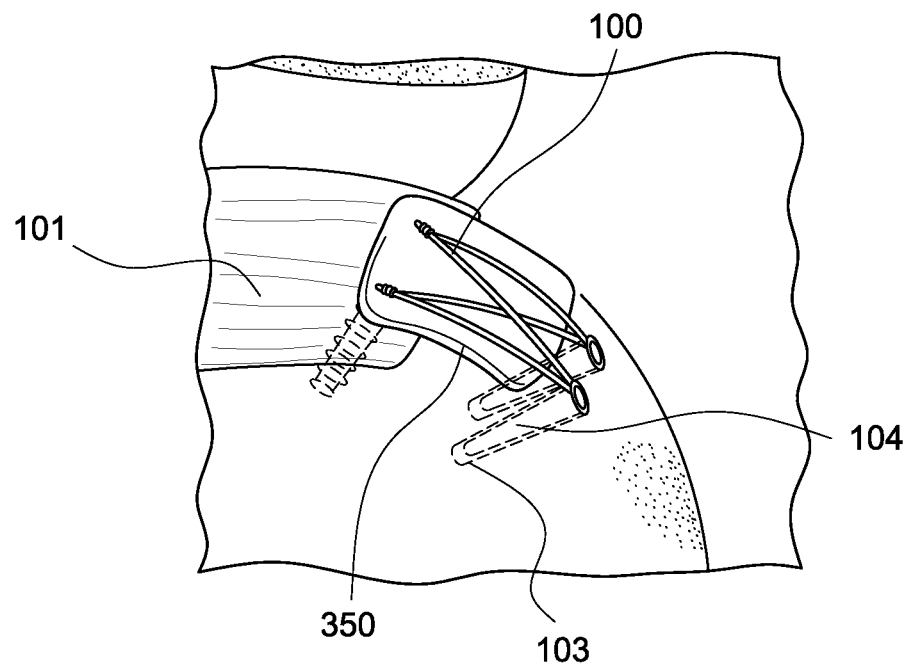

Referring now to FIGS. 15-16, the hydrated collagen patch 250, 350 can be positioned under or above a tissue 101, depending upon the characteristics of the repair site and of the damaged tissue. Various techniques may be used to re-attach the tissue 101 and hydrated collagen patch 250, 350. One reattachment technique is the SutureBridge™ Technique, recently introduced by Arthrex, Inc., which is described in U.S. patent application Ser. No. 11/700,916 filed on Feb. 1, 2007, the disclosure of which is hereby incorporated by reference in its entirety. The BMA-hydrated collagen patch 250, 350 helps to promote healing and reattachment of the tissue to bone, and is eventually incorporated into the cellular tissue.

In the SutureBridge™ Technique, two pilot holes (not shown) are formed in an articular margin of the humerus. Subsequently, two suture anchors 102 are placed in the two pilot holes (not shown) in a medial row. Two pilot holes 103 for the knotless fixation devices 104 are formed approximately 5-10 mm distal to the lateral edge of the greater tuberosity. Sutures 100 in a criss-cross arrangement, over the collagen patch 250, 350, are held by the suture anchors 102 and the knotless fixation devices 104.

Alternatively, after arthroscopic controlled BMA harvest, the BMA is injected with a hypodermic needle into the tissue to tissue or tissue to bone surgical repair site of the respective joint of harvest without orthobiologic carriers. For example, a small PVC tube with multiple side perforations (up to 1 cm for tube end) may be inserted under the cuff prior to or after the SutureBridge™ repair. A luer lock connection to the BMA syringe facilitates BMA injection under the completed repair site and pulled from the portal at the end of the case in the absence of pressurized saline to disburse BMA. Coagulates may be added to the syringe before insertion to prevent further migration. Once the BMA is injected, the tube is removed from the repair site.

Figure 17:
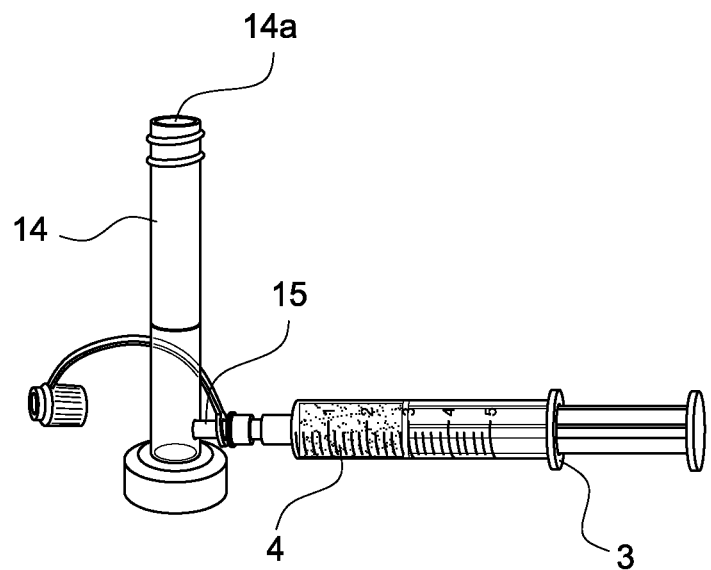
FIGS. 17-22 illustrate the sequence steps for using a cannula to transfer and deliver extracted bone marrow aspirate, according to a preferred embodiment of the present invention.
Figure 18:
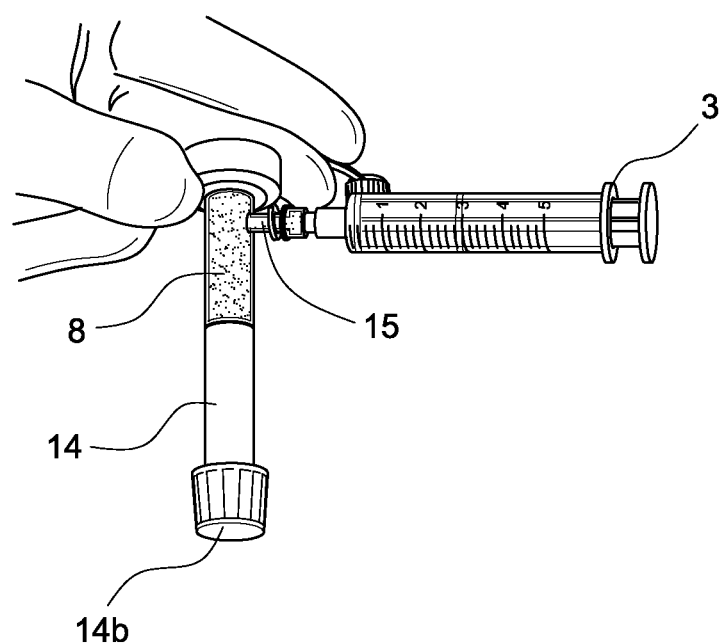
Figure 19:
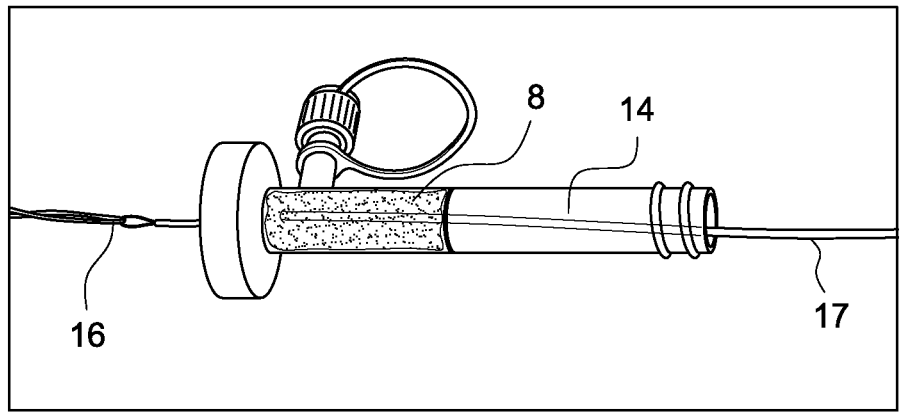
Figure 20:
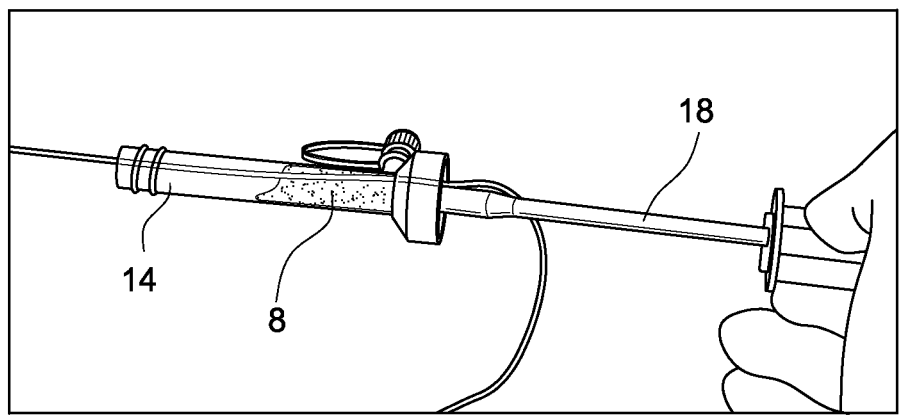
Figure 21:
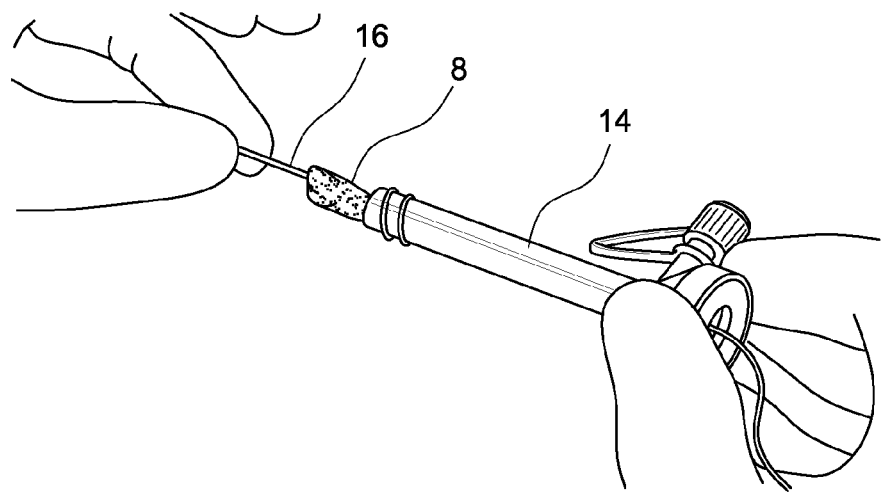
Figure 22:
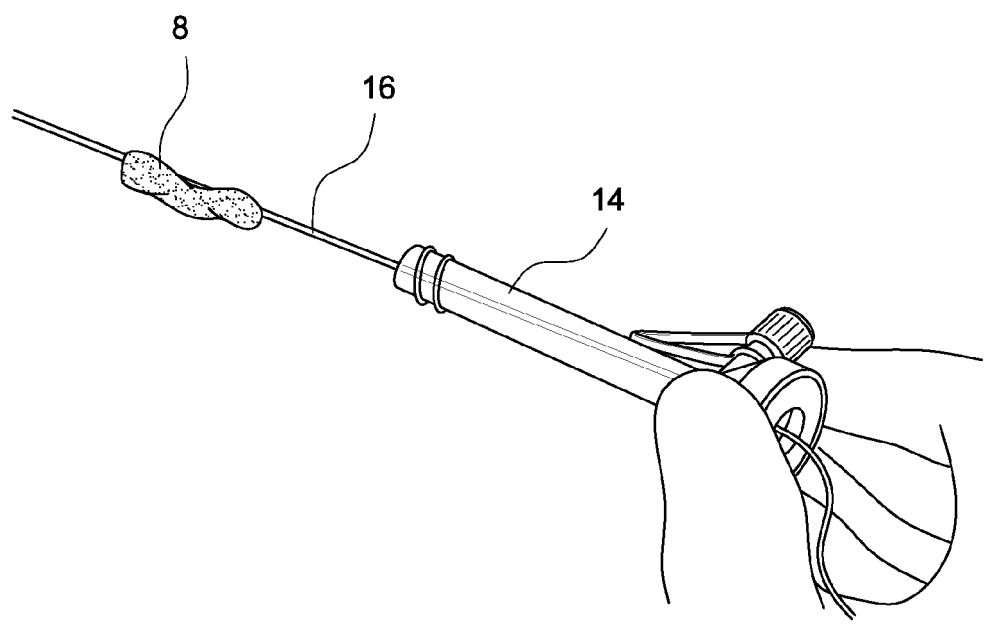

Another alternate embodiment provides using a cannula 14 as a clot mold and delivery system for coagulated BMA. First, the cannula 14, preferably a clear, 7 mm or 8.25 mm Partially Threaded Cannula, is placed with dam end down on a sterile table. Various diameter cannulas may be used to form various clot sizes. Next, as illustrated in FIG. 17, BMA 4 is injected into the luer lock side port 15. Then, a clotting solution is added to the BMA 4 from the top 14a of the cannula 14. The coagulant may be added to the cannula 14 from the side port (using a 1 cc syringe) before the BMA 4 is added. It is preferable to add about 0.25 cc of reconstituted 1000 IU/ml thrombin solution to 2.5 cc of BMA. This can vary slightly depending on the desired clot size, however the ratio will remain the same. If needed, a cap 14b (FIG. 18) is placed on the end of the cannula 14 to hold the BMA 4 and clotting agent in place during solidification. The cannula 14 can stand upright on the table to contain the BMA 4 during clot setting, without using a distal plug. The dam keeps the clot better contained and prevents fluid intrusion during delivery. After some time, about 2-3 minutes, a clot 8 is formed as shown in FIG. 18. The empty syringe 3 should be in the side port 15 until the blood coagulates. After coagulation, the syringe 3 can be removed and the port 15 capped. Then, as illustrated in FIG. 19, a suture 16 is passed through the clot 8 using a needle 17, such as a long meniscal needle. Using an obturator 18, the clot 8 is loosened in the cannula 14 as shown in FIG. 20. FIG. 21 shows the removal of the clot 8 from the cannula 14 by pulling on the suture 16. After removal from the cannula 14, the clot 8 is on the suture 16, shown in FIG. 22, and may be placed at the desired site to promote healing.

Alternatively, once the clot 8 is formed in the cannula 14, the cannula 14 can be inserted into the joint (not shown) for delivery of the clot 8. To advance the clot 8 in the joint, an obturator 18 is inserted through the dam. A long meniscal needle 17 could be inserted through the cannula 14 and clot 8 before delivery to provide suture 16 tethered control of the clot 8 in the joint. The suture 16 and clot 8 can be secured with knots or anchors or suture 16 pulled out after placement. The SutureBridge™ Technique, discussed above, may also be used to secure the clot 8 to promote healing of a tissue.

Figure 23:
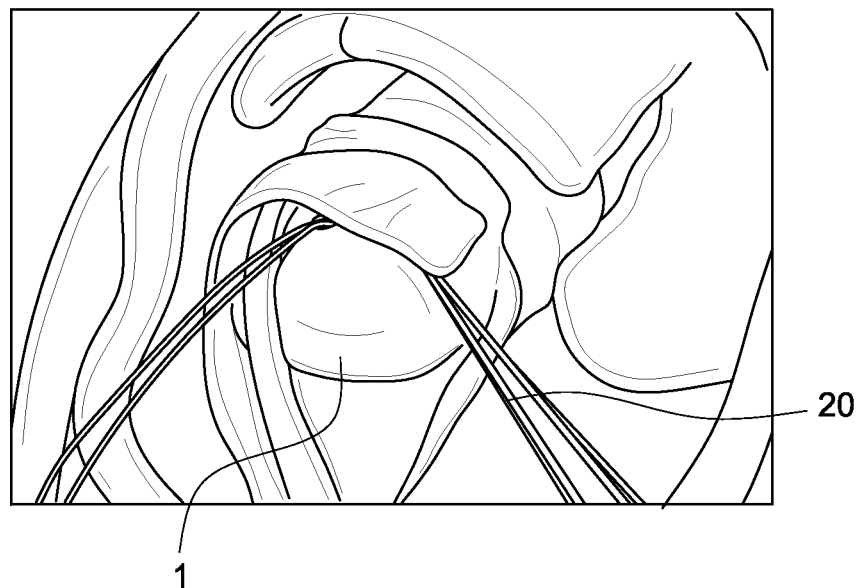
FIGS. 23-31 illustrate the sequence steps of a button technique for bone marrow aspiration, according to a preferred embodiment of the present invention.
Figure 24:
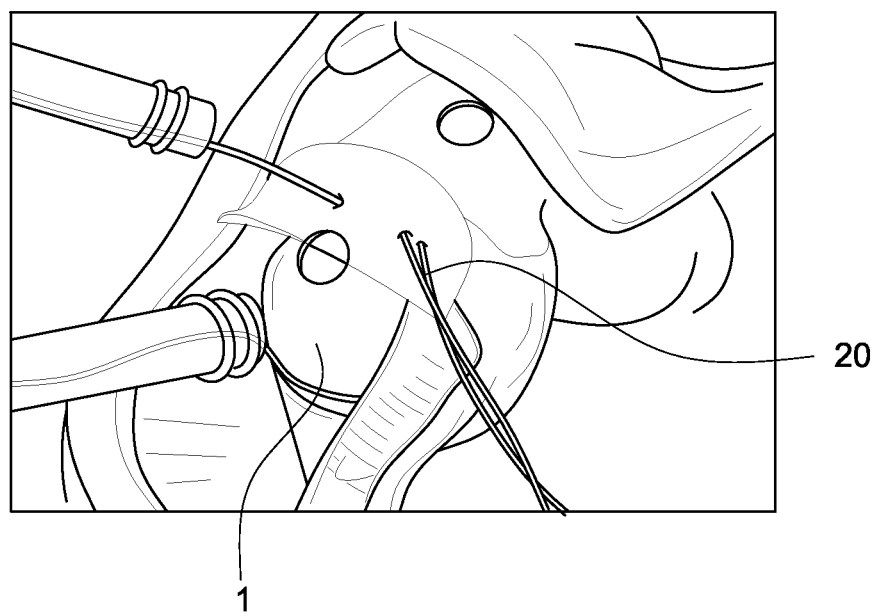
Figure 26:
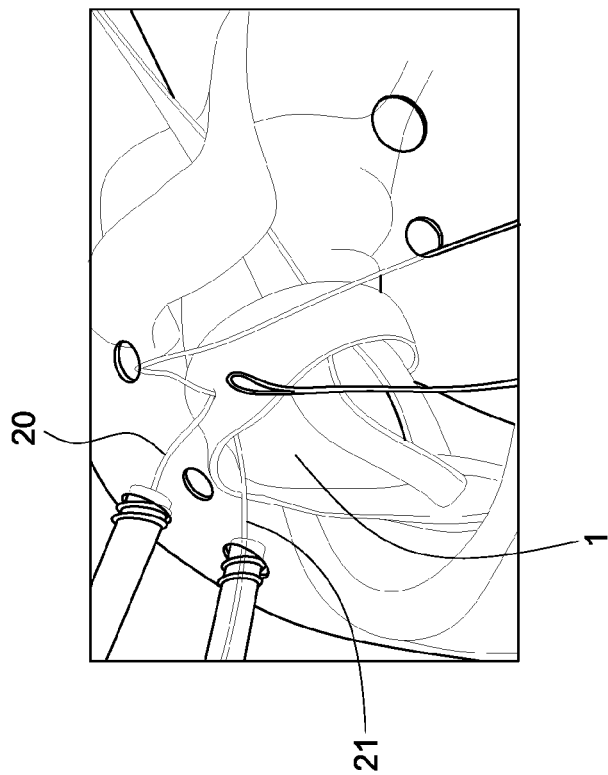
Figure 25:
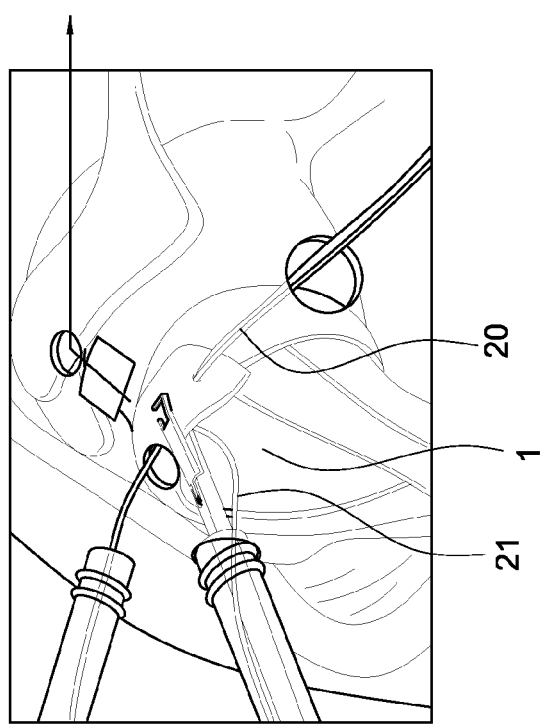
Figure 28A:
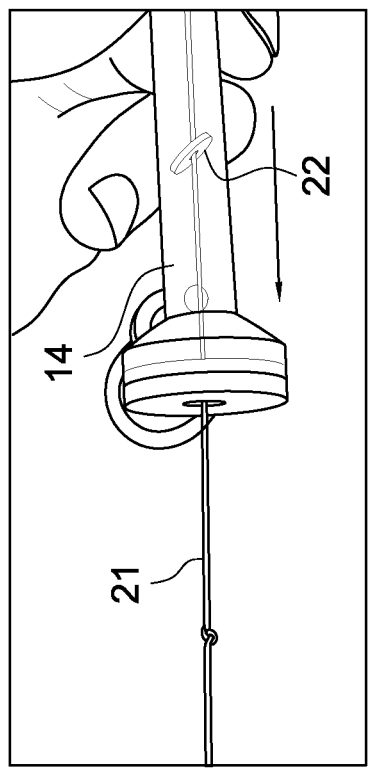
Figure 27:
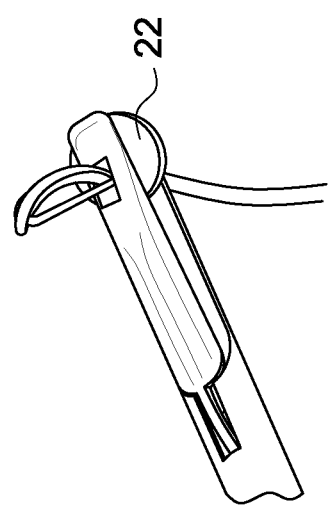
Figure 28B:
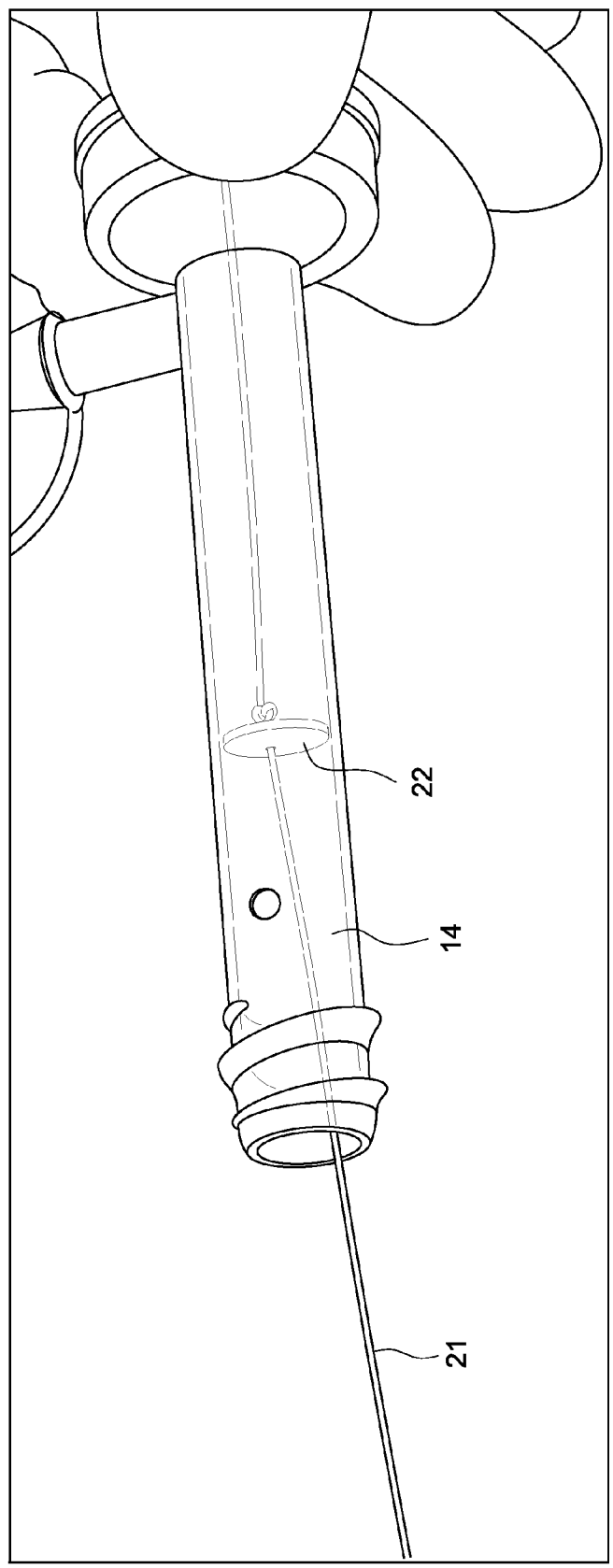
Figure 29:
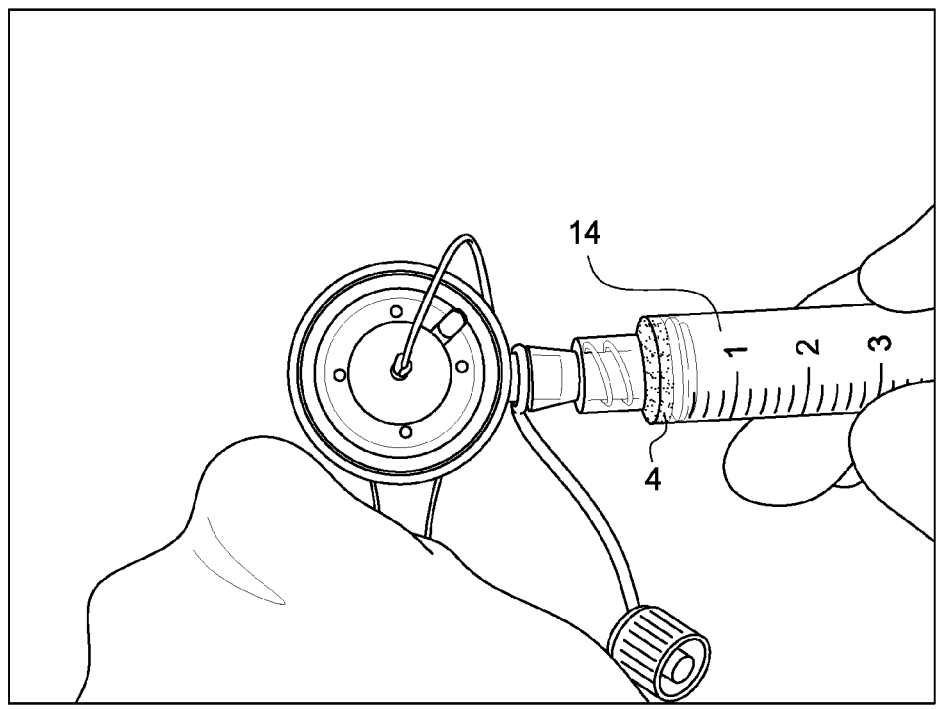
Figure 30:
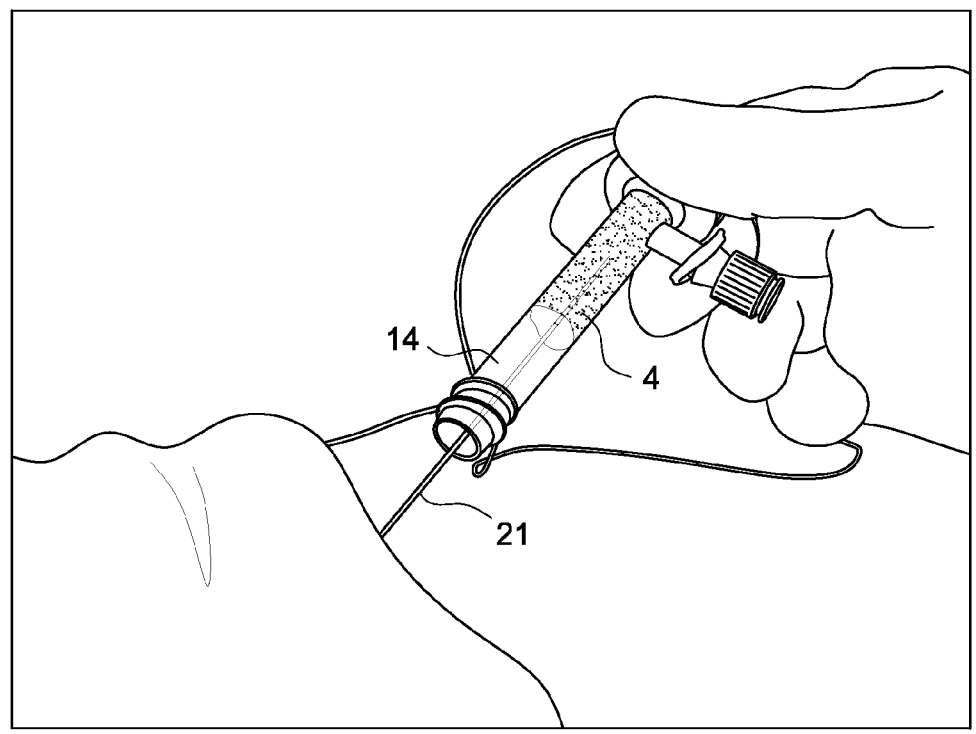
Figure 31:
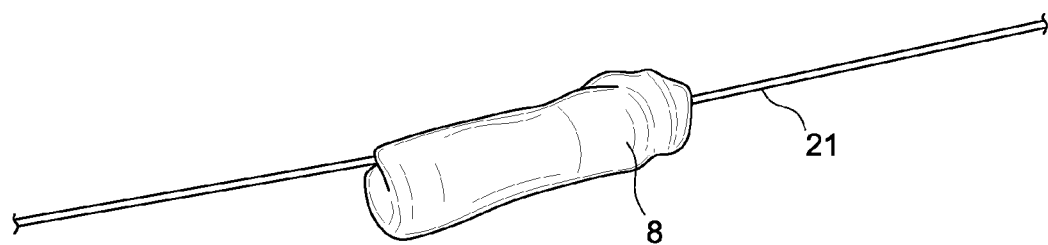

Alternatively, a button technique can be used as shown in FIGS. 23-31. Although the button technique shown in FIGS. 23-29 is illustrated with a human shoulder, it should be understood that the technique can be used in a human knee joint. In FIGS. 23-24, a medial row (not shown) is inserted. A suture 20 is removed from each anchor and passed through the cuff 1 and moved to anterior and posterior portals. Knots should not be tied in the suture 20. As shown in FIGS. 25-26, a new suture, a "clot suture," 21 is passed through a lateral cannula and passed through the cuff 1 between the medial anchors before finally being removed through the superior incision. As shown in FIGS. 27-28, a button 22 (e.g., about 8 mm in diameter) from the collagen patch is punched out using an OATS coring device. The lateral cannula is removed and the clot suture 21 is used to pass through a hole in the center of the button 22. The button is then pulled through a cannula 14 (e.g., about 8.25 mm in diameter) all the way to the dam. A knot is tied in the suture 21 to prevent the suture 21 from sliding through the button 22 and to allow removal of the suture 21 once the clot is in place.

The BMA 4 is then clotted in the cannula 14 on a collagen patch, as discussed above and illustrated in FIGS. 29-31. The BMA clot 8 is then pulled under the cuff 1. The medial end of the clot suture 21 is pulled. The cuff 1 may be lifted, if necessary. The button 22 will guide the clot 8 in place under the cuff 1. A medial row is tied, if reattaching tissue using the SutureBridge™ Technique, as mentioned above. The button 22 may be separated from the clot 4 or the button 22 may be left under the cuff 1. Then, the SutureBridge™ is completed by placing the lateral row. Once completed, the button 22 may be removed. To remove the button 22, an additional medial knot should have been tied on the clot suture 21.

Although the present invention has been described in relation to particular embodiments thereof, many other variations and modifications and other uses will become apparent to those skilled in the art.

What is claimed is:

1. A method of harvesting and therapeutic application of bone marrow aspirate, comprising:
    establishing a portal proximal to a human joint using a trocar;
    inserting an aspiration needle through the portal into the joint and into a surgical site of a bone of the joint and, subsequently, removing the trocar;
    connecting a first syringe to the aspiration needle and, subsequently, aspirating bone marrow from the surgical site of the bone of the human joint using the first syringe;
    transferring the bone marrow into a tray containing a biomaterial to hydrate the biomaterial with the bone marrow and to obtain a hydrated biomaterial;
    applying the hydrated biomaterial with the bone marrow to the same surgical site of the same human joint through an arthroscopic procedure; and
    securing the hydrated biomaterial with the bone marrow at the human joint by placing suture over the hydrated material with the bone marrow, and securing the suture with fixation devices to the bone,
    wherein the steps of aspirating and applying bone marrow from and to the same surgical site of the human joint are conducted arthroscopically.

2. The method of claim 1, wherein the biomaterial comprises collagen.

3. The method of claim 1, wherein the human joint comprises one of a shoulder joint, a hip joint, an elbow joint, and a knee joint.

4. The method of claim 1, wherein the biomaterial is a patch and wherein the method further comprises the steps of hydrating the patch with the bone marrow to obtain a bone marrow aspirate patch and delivering the patch to an injured tissue.

5. The method of claim 4, wherein the step of delivering the patch further comprising:
    passing the suture through a lateral cannula and through a rotator cuff of a shoulder joint, the suture having the patch on one end and a button on another end;
    pulling the suture to place the patch under a tissue; and
    pulling the button through the lateral cannula and subsequently, securing the suture in a criss-cross arrangement using knotless fixation devices and suture anchors.

6. The method of claim 1, further comprising the step of adding a clotting agent to the bone marrow to form a clot subsequent to the step of transferring the bone marrow into a tray.

7. The method of claim 6, wherein the clotting agent comprises calcium salt comprising calcium chloride solution having a concentration of about 10%.

8. The method of claim 6, wherein the clotting agent comprises thrombin solution having a concentration of 1000 I.U./ml.

* * * * *